United States Patent [19]

Chou et al.

[11] 4,013,943
[45] Mar. 22, 1977

[54] SOLID STATE ELECTROLYTIC CELL GAS SENSOR HEAD

[76] Inventors: Jack Chou; Doris H. Chou, both of 900 N. Broadway, Suite 725, Santa Ana, Calif. 92701

[22] Filed: June 10, 1976

[21] Appl. No.: 694,840

Related U.S. Application Data

[63] Continuation-in-part of Ser. No. 505,546, Sept. 13, 1974, Pat. No. 3,955,268.

[52] U.S. Cl. .............................. 324/33; 324/71 SN; 338/34; 73/27 R; 340/237 R; 23/232 E; 23/254 F
[51] Int. Cl.$^2$ .................. G01N 27/00; H01L 7/00; G01N 27/62
[58] Field of Search ........... 324/33, 71 SN; 338/34; 73/27 R; 340/237 R; 23/232 E, 254 E

[56] References Cited

UNITED STATES PATENTS 3,865,550 2/1975 Bott et al. ................... 73/27 R X
3,911,386 10/1975 Beaudoin et al. ................. 338/34

*Primary Examiner*—Rudolph V. Rolinec
*Assistant Examiner*—Vincent J. Sunderdick

[57] ABSTRACT

A Solid State Electrolytic Cell Gas Sensor is presented which is capable of measuring various toxic or combustible gases in low concentrations (0–5 PPM) up to and including high concentrations such as 0–20 percent by volume. The sensor exhibits excellent specificity to the gas designated to be detected. The sensor causes the dissociation of the gases into charged species such as ions and complex ions and does not operate by changing its electro-conductivity in response to the adsorption of the gas. The sensor has an electrical signal which is a function of the type and concentration of gas and which is also a function of the collection of ions by transport process. The solid state material from which the sensor is fabricated is produced by the method of addition of one or more metal oxides to a non-metal oxide with a general formula of $M_xO_y - N_pO_q$. M can be a metal from the transition elements and N can be a non-metal of group III and IV from the periodic table. The sensor comprises a collector and a heater element made from a stable metal such as platinum. A material such as stannic oxide may be mixed with a material such as silica gel. The combination may be heated and dried and dissolved in an alcohol and water solution. The resulting combination is then coupled to the heater wire and to the collector wire and heated to form the finished sensor.

9 Claims, 2 Drawing Figures

SOLID STATE ELECTROLYTIC CELL GAS SENSOR HEAD

The present application is a continuation in part of applicant's previous application filed Sept. 13, 1974, Ser. No. 505,546, now U.S. Pat. No. 3,955,268, entitled (after requirement to restrict) METHOD OF FABRICATING AN ELECTROLYTIC CELL GAS SENSOR.

BACKGROUND OF THE INVENTION

1. Field of the Invention

The present invention relates to sensors which detect toxic or combustible gases by causing the dissociation of the gases into charged species such as ions and complex ions.

2. Description of the Prior Art

The prior art includes a number of catalytic sensing elements in which a platinum wire is coated with catalytically activated ceramic materials. The platinum wire is heated to a high temperature. In the presence of combustible gas, the platinum wire raises the temperature. The positive coefficient of temperature resistance of the platinum wire which increases the resistance of the wire therefore can be used as a signal to detect combustible gas. This method has been in use for the last quarter century but has a disadvantage in that the element will burn out in high gas concentrations. The gas to air mixture has to be in the right combustible mixture. In the upper explosive region the sensor is inactivated because of a lack of oxygen. This weakness endangers nearby life and properties. In addition, catalytic activity decreases in the presence of certain impurities such as low concentrations of $H_2S$. In addition, it will not detect gas in low ppm range.

In recent years, a semiconductor gas sensor generated great interest. This sensor, in general, consists of various ceramic material. In the processing of this ceramic, a non-ceramic material is added which evaporated when heated, thereupon creating a porous sintered structure in the ceramic. In the presence of certain air impurities, the gas molecules are absorbed by this sintered ceramic which changes its electroconductivity. This method obtains very interesting results as far as obtaining high sensitivity to gas goes. But in practical application it cannot offer any accuracy in quantitiative determination of the gases. It is also without any specificity to any cases. So accordingly, it cannot be used as a monitoring device. In addition, prior methods of gas detection include chemical tapes, chemical gels, wet chemical instruments, and other devices. All of these are based upon different theories or principals of operation than electrolytic cell sensor.

Unfortunately, all of the prior art detectors have one or more of the following disadvantages:

1. Some of them burn out when exposed to high concentrations of gases;
2. Some of them are poisoned and thus rendered useless by toxic gases;
3. Some of them are incapable of measuring low concentrations of impurities or high concentrations of impurities or both;
4. Some of them have an extremely short life;
5. Some of them are effected by differences in temperature or attitude;
6. Some of them require a vacuum or other pump to circulate the gas sample;
7. Some of them require five, ten or even sixty minutes to respond.

The prior art, such as the Bott et al. patent 3,865,550, discloses a semi-conducting element whose electrical conductivity is dependent upon the concentration of the gas in the atmosphere. Prior to applicant's original application, the prior art does not disclose any sensor which caused the dissociation of the gases to be measured into charged species such as ions and complex ions.

SUMMARY OF THE INVENTION

A Solid State Electrolytic Cell Gas Sensor and a method of producing the sensor are presented. The sensor is capable of measuring various toxic or combustible gases in low concentrations such as 0–5 PPM as well as high concentrations such as 0–20 percent by volume with excellent specificity to the gas designated to be detected. The Solid State material is fabricated by addition of one or more metal oxides to a non-metal oxide with a general formula of $M_xO_y - N_pO_q$. (Where M is a metal from the transition elements and N is a non-metal of group III or IV from the periodic table.

The sensor operates by means of the dissociation of the gases which are to be detected into charged species such as ions and complex ions. The ions are then used to generate an electrical signal by transport process between two wires in the semi-conductor material.

It is well known that when the proper amount of energy is applied to a gas molecule, the gas molecule will dissociate into charged species whereby a material having a general formula of $M_xO_y - N_pO_q$ where M is a metal from the transition elements and N is a non-metal of group III or IV causes a specific crystal structural arrangement in which a gas can be detected more specifically than by prior art methods of gas sensing elements.

The sensor comprises a collector element and a heater element made from stable metal such as a member of the platinum family. The collector wire can be of 5 mil diameter and 6 turns helix coil. The heater element can be 2 mil in diameter and 10 turn coil. The heater element is maintained inside the collector wire by the metal oxide materials. The external surface of the sensor is totally covered by the metal oxide. Alternatively, the collector can be a plate instead of a coil. The plate can be fabricated from a foil of the platinum family or a coil smashed down to become a plate.

In operation, between 150 ma and 200 ma of electrical current is passed through the heater coil, which in turn heats the whole sensor element to about 300°–400° F. At this temperature, which is called operational temperature, the sensor is activated for gas sensing.

To fabricate a sensor according to the method of the present invention, mix tin oxide in the form of stannic oxide and silica gel made from sodium silicate in the ratio 6:1. Two parts of alcohol and one part of water is mixed to use as a solvent and added to the combination of stannic oxide and silica gel. The solvent is added in such a quantity that the resulting mixture is a paste. Sufficient $Pt_2O$ is stirred into the mixture so that the final mixture is a paste which can be easily coated on coils of platinum or similiar metal. For most purposes, approximately 2 percent $Pt_2O$ is sufficient.

The paste may be coated to the heater coil first. The coated heater may be inserted into the collector wire which is then coated with more paste to form a smooth round bead. If it is desired to fabricate a collector plate, the plate is then attached to the coated heater and more paste mixture is applied to form a smooth bead.

The finished head is then heated under infra-red light for 48 hours, then moved into a oven at approximately 250° C for four hours. The oven temperature may then be increased to about 450° C for another hour. Finally, the oven temperature may be raised for another hour to approximately 600° C.

A sensor prepared according to applicant's invention differs from the prior art in that the prior art comprises a semi-conductor whose electrical conductivity is dependent upon the concentration of the gas in the atmosphere. A sensor prepared according to the present invention causes a dissociation of the gases or gas to be measured into charged species such as ions and complex ions and does not operate by changing its electro-conductivity in response to the adsorption of a particular impurity or combination of impurities. The difference between a sensor according to the present invention and a sensor which changes in electro-conductivity is somewhat similar to the difference between causing a given number of charged particles to pass between selected points by reducing the resistance of the electrical conductivity between the two points and (as illustrative of the present invention) dissociating impurities so that there are more ions or complex ions which can begin to make the trip, thereby permitting completion of the trip by a larger number of ions. The difference is somewhat analogous to preparing a system which permits a greater percentage of a collected number of ion to pass between two points to a system which permits a lessor percentage of a greater number of ions to pass between two points.

DRAWING DESCRIPTION

Reference should be made at this time to the following Detailed Description which should be read in conjunction with the following drawings, or which:

FIG. 1 illustrates an example of the invention utilizing coiled heater and collector wires; and FIG. 2 illustrates a second example of the invention utilizing a collector plate.

DETAILED DESCRIPTION

Figure 1:
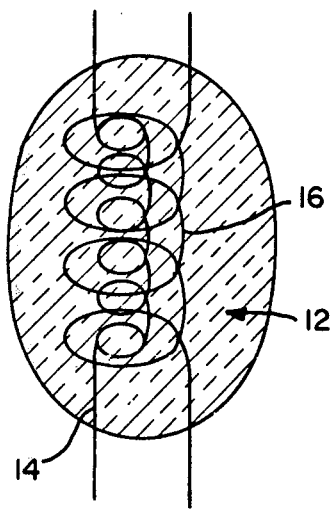

Reference should be made at this time to FIG. 1 which illustrates a solid-state electrolytic cell gas sensor 10 according to the present invention. The sensor 10 comprises a base 12 having coupled thereto a heating and power wire 14, and a collector wire 16.

Various examples of the invention are posssible. Either AC or DC power can be utilized. In a first example, one end of the heating wire 14 is coupled to a DC source of approximately +9 volts. The opposite end of the heating wire 14 may be grounded through a relatively low value current limiting resistor.

One end of the collector wire 16 may be open, while the opposite end is coupled to a meter which in turn is coupled to an appropriate alarm.

The base 12 should be fabricated from inert material capable of being penetrated by gases and having a high resistance in the absence of ions and complex ions, and a lower resistance in the presence of ions and complex ions. The base 12 may be fabricated from one or a combination of more than one of the following ceramic materials: $Al_2O_3$, $SnO_2$ and ZnO. Other ceramic materials having a resistent change by a factor greater than five in the presence of ions and complex ions or relatively inert electrolyte materials may also be used.

The heating wire may be fabricated from a fine, chemically inert, strong and ductile material such as platinum, palladium, other members of the platinum family, or other similar material. If a platinum family material is used, the wire should be drawn to approximately 2 mils, thereby giving the wire a resistance of approximately 9 ohms within the base thereby generating enough heat to maintain the base at a temperature of approximately 200° F to 400° F. A current limiting resistor of approximately 50 ohms couples the heating wire to the ground and insures the correct amount of heating.

The temperature reached by the base during operation is increased by increasing the length of heating wire within it, by decreasing the value of the current limiting resistor, by decreasing the diameter of the heating wire within it, and by increasing the voltage from the power supply. An operating, temperature of approximately 300° F is suitable for the detection of pollutants such as $H_2S$ and CO. For more stable pollutants, such as hydro carbons, the temperature of the base during operation should be approximately 400° F. The temperature of the base must be maintained at a higher temperature in order to detect pollutants which are more difficult to ionize.

The base 12 material, together with the high temperature, causes the pollutant to ionize within the base 12. Since the base is activated, the gas can enter the base and the ratio of pollutants within the base is a function of the ratio of pollutants in the air or other medium surrounding the base 12.

The collector wire 16 comprises a fine collector electrode disposed in the base 12 a short distance from the heating wire 14 and coupling the base 12 to the return of the direct current source. The collector wire or electrode 16 may be coiled. The collector electrode 16 may have an end disposed in the base 12 which end is coiled and smashed flat in order to permit easier fabrication of the sensor 10. Since the resistance between the heating wire 14 and the collector wire 16 is relatively critical, coiling the end of the collector wire 16 and smashing it flat makes it easier in certain cases to fabricate the sensor with the selected required resistance.

A collector electrode 16 diameter of about 5 mils is sufficient. The collector wire 16 should be disposed a sufficient distance from the heating wire 14 so that the resistance between them exceeds 100,000 ohms. For most purposes, a resistance between the heating wire 14 and a collector wire 16 of approximately 150,000 ohms in the absence of ions and complex ions is sufficient. In the presence of ionized pollutant which would comprise ions and complex ions, the resistance between the heating wire 14 and the collector wire 16 is reduced to less than 10,000 ohms, thereby causing a more than 10 fold increase in current flow between the heating wire 14 and the collector wire 16. A relatively small number of ions or complex ions can greatly reduce the resistance, so that the drop in resistance is very sharp and quick as the amount of pollutant in the air approaches the predetermined limit.

One end of the collector wire 16 is open. The other end of the collector wire 16 is coupled to an alarm trigger circuit which may comprise any of the prior art types of meters capable of detecting changes in signal flow. When the amount of pollutant approaches one part in a million, or the other predetermined limit, the pollutant also infiltrates the electrolyte base 12 where it is ionized, causing a sharp increase in signal flow through the collector wire 16 to the meter. The meter detects the increase in current and triggers an appropriate alarm.

Figure 2:
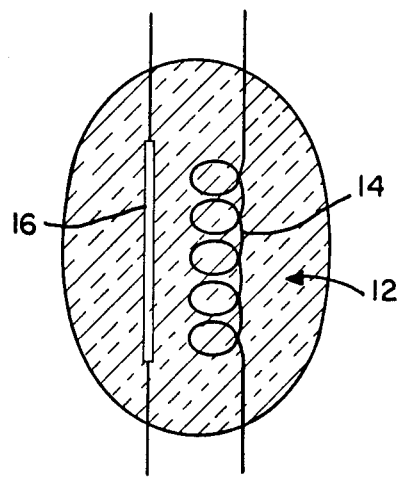

Reference should be made at this time to FIG. 2 which illustrates a slightly modified example of the invention 10. As previously indicated, the collector can be smashed flat to form a plate. An alternative example would permit the use of a plate 16 of foil as illustrated in FIG. 2. The electrical component such as meters, alarms, resistors, are not illustrated in FIGS. 1 and 2 which illustrate the components of the present invention which differ from the prior art.

The method of fabricating a solid state electrolytic cell gas sensor head capable of dissociating impurities into species such as ions and complex ions comprises adding at least one metal oxide having a general formula $M_xO_y$, where M is a transition element metal, to a non-metal oxide having a general formula $N_pO_q$, where N is a non-metal selected from groups III and IV of the periodic table, and $x, y, p, q$ are relatively small whole numbers. $Al_2O_3$, $SnO_2$ and ZnO, as well as other transition element metal oxides are very suitable. If stannic oxide is used, it may be mixed with silica gel which may be made from sodium silicate in a ratio of approximately 6:1. The mixture is then dried and activated. Temperatures of 200° C – 300° C are suitable for drying and activating most mixtures suitable for use in the present invention. A sufficient quantity of solvent such as two parts of alcohol and one part of water mixed together is added to the mixture. A sufficient quantity of solvent is added so that the resulting mixture is a paste. A small amount of an oxide of the platinum family is then stirred into the paste. The exact amount is not very important, however, a sufficient amount has to be added so that the final mixture is a paste which can be easily coated on a coil. Two percent $Pt_2O$ is suitable for most pastes.

The paste is then coated to a fine, chemically inert, strong and ductile heating wire which may comprise a platinum family wire 2 mils in diameter and 10 turn helix coil.

The coated heater may then be inserted into a collector wire which may comprise 5 mils in diameter and 6 turns helix coil fabricated from metal of the platinum family. Paste may then be added to the wires to form a sensor head completely covering the segment of the collector wire having heating wire inserted therein so that the space within the coils of collector wire is filled with paste.

Alternatively, the collector may comprise a plate fabricated from a platinum family foil or the collector coil may be smashed down to form a plate. The sensor head is then dried and baked at at least one temperature in excess of 200° C. One useful sequence is drying the sensor head under infra-red light for 48 hours, then baking in an oven at 250° C for four hours, then baking in the oven at 450° C for one hour, then baking in the oven at 600° C for one hour.

The paste dries and hardens into a relatively inert, porous semi-conducting base material, capable of dissociating impurities into species such as ions and complex ions. The heating coil is then coupled to a source of direct current. Platinum and palladium are both particularly suitable materials to use for the wires and plates used in the present invention. The collector electrode is disposed in the base a short distance from the heating wire and couples the base material of the head to the return of the direct current source.

In operation, the direct current source may comprise a current source between 150 ma and 200 ma which will be sufficient to heat the sensor to between 300° F and 400° F. The collector may be coupled to appropriate alarm means to set off an alarm when the signal exceeds the selected amount.

A particular example of the invention has been described herein. Other examples within the scope of the described invention will be obvious to those skilled in the art. The invention is limited only by the following claims:

We claim:

1. A solid state electrolytic cell gas sensor head which causes the dissociation of gaseous impurities to be measured into charged species such as ions and complex ions and does not operate by changing the electro-conductivity of the sensor head in response to the adsorption of at least one gaseous impurity, comprising:
   a relatively inert, electrolyte base material, capable of dissociating selected impurities into species such as ions and complex ions;
   a signal source;
   a fine, chemically inert, strong and ductile heating wire coupling signals from the signal source to the base; and
   a fine collector electrode disposed in the base a short distance from the heating wire, electrically coupled to the heating wire by means of ions and complex ions dissociated by the base and capable of collecting the signal.

2. The invention of claim 1 further including a meter coupled to measure the signal passing through the sensor, and a 9 vdc source which generates a direct current between 150 ma and 200 ma which current heats the sensor head to between 300° F and 400° F.

3. The invention of claim 2 further including alarm means coupled to the collector to set off an alarm when the signal exceeds a preselected amount.

4. The invention of claim 1 wherein the collector electrode disposed in the base is coiled.

5. The invention of claim 4 wherein the collector electrode has an end disposed in the base which end is coiled in a flat coil.

6. The invention of claim 1 wherein the resistance between the heating wire and the collector electrode is reduced by a factor greater than five in the presence of ions and complex ions.

7. The invention of claim 1, wherein the heating wire and the collector electrode each have diameters within the range of 2–5 mils.

8. The invention of claim 1, wherein the wire and the electrode are fabricated from a platinum family metal.

9. The invention of claim 1, wherein the base is fabricated from one of the following ceramic materials: $Al_2O_3$, $SnO_2$ and ZnO.

* * * * *